United States Patent
Burdea et al.

(10) Patent No.: US 12,347,548 B2
(45) Date of Patent: Jul. 1, 2025

(54) MEDICATION ENHANCEMENT SYSTEMS AND METHODS FOR COGNITIVE BENEFIT

(71) Applicant: Bright Cloud International Corporation, Highland Park, NJ (US)

(72) Inventors: Grigore C. Burdea, Highland Park, NJ (US); Edward A. Berde, Princeton, NJ (US)

(73) Assignee: Bright Cloud International Corporation

( * ) Notice: Subject to any disclaimer, the term of this patent is extended or adjusted under 35 U.S.C. 154(b) by 454 days.

(21) Appl. No.: 16/818,964

(22) Filed: Mar. 13, 2020

(65) Prior Publication Data

US 2020/0294652 A1    Sep. 17, 2020

Related U.S. Application Data

(60) Provisional application No. 62/817,962, filed on Mar. 13, 2019.

(51) Int. Cl.
*G16H 20/70*    (2018.01)
*A61B 5/00*    (2006.01)
(Continued)

(52) U.S. Cl.
CPC ......... *G16H 20/70* (2018.01); *A61B 5/0022* (2013.01); *A61B 5/163* (2017.08); *A61B 5/165* (2013.01);
(Continued)

(58) Field of Classification Search
CPC ........ G16H 20/70; G16H 40/67; G16H 50/50; G16H 50/20; G16H 20/10; A63F 13/213;
(Continued)

(56) References Cited

U.S. PATENT DOCUMENTS 10,380,321 B2 *  8/2019  Kamen ................. G16H 40/63
10,694,990 B2    6/2020  Burdea et al.
(Continued)

OTHER PUBLICATIONS

Jerome I. Rotgans et al., "Cognitive engagement in the problem-based learning classroom" Adv in Health Sci Educ (2011) 16:465-479, DOI 10.1007/s10459-011-9272-9, Published online: Jan. 18, 2011, pp. 466-479.
(Continued)

*Primary Examiner* — Malina D. Blaise
(74) *Attorney, Agent, or Firm* — The Belles Group, P.C.

(57) ABSTRACT

Systems and methods for providing cognitive therapy to a patient are provided, which include a head mounted device wearable by the patient, a display configured to present one or more cognitive game scenes to the patient, one or more controllers for interacting with the cognitive training scenes, a cognitive engagement detection device configured to detect cognitive engagement of the patient and generate data indicative of the cognitive engagement of the patient, and a processor. The processor determines a level of cognitive engagement of the patient based at least in part on the data generated by the cognitive engagement detection device, determines performance of the patient interacting with the one or more cognitive training scenes based on information received from the one or more controllers, and determines cognitive improvement of the patient based on the cognitive engagement, cognitive medication taken, and the performance of the patient.

11 Claims, 17 Drawing Sheets

(51) Int. Cl.
    *A61B 5/16*     (2006.01)
    *A63F 13/213*     (2014.01)
    *G09B 5/02*     (2006.01)
    *G09B 19/00*     (2006.01)
    *G16H 20/10*     (2018.01)
    *G16H 40/67*     (2018.01)
    *G16H 50/20*     (2018.01)
    *G16H 50/50*     (2018.01)

(52) U.S. Cl.
    CPC .......... *A61B 5/4088* (2013.01); *A61B 5/4848* (2013.01); *A61B 5/6803* (2013.01); *A63F 13/213* (2014.09); *G09B 5/02* (2013.01); *G09B 19/00* (2013.01); *G16H 20/10* (2018.01); *G16H 40/67* (2018.01); *G16H 50/20* (2018.01); *G16H 50/50* (2018.01)

(58) Field of Classification Search
    CPC ....... A61B 5/163; A61B 5/0022; A61B 5/165; A61B 5/4088; A61B 5/4848; A61B 5/6803; G09B 5/02; G09B 19/00
    See application file for complete search history.

(56) References Cited

U.S. PATENT DOCUMENTS

| | | | |
|---|---|---|---|
| 2012/0136274 A1* | 5/2012 | Burdea | A63F 13/28 600/545 |
| 2013/0317753 A1* | 11/2013 | Kamen | G16H 40/20 600/595 |
| 2016/0270718 A1* | 9/2016 | Heneghan | A61B 7/003 |
| 2017/0231490 A1* | 8/2017 | Toth | G16H 40/63 600/558 |
| 2018/0203238 A1* | 7/2018 | Smith, Jr. | G02B 27/017 |
| 2019/0159716 A1* | 5/2019 | Alailima | A61B 5/165 |
| 2019/0216392 A1* | 7/2019 | Bower | A61B 5/168 |
| 2019/0261908 A1* | 8/2019 | Alailima | G09B 7/02 |
| 2020/0060603 A1* | 2/2020 | Bower | A61B 5/167 |
| 2020/0174557 A1* | 6/2020 | Alailima | A61B 5/4884 |
| 2020/0380882 A1* | 12/2020 | Alailima | A61B 5/4836 |
| 2021/0290148 A1* | 9/2021 | Najafi | G16H 40/63 |
| 2024/0081706 A1* | 3/2024 | Alailima | A61B 5/7455 |

OTHER PUBLICATIONS

Roee Holtzer et al., "Cognitive Fatigue Defined in the Context of Attention Networks", Neuropsychol Dev Cogn B Aging Neuropsychol Cogn. Jan. 2011 ; 18(1): 108-128. doi: 10.1080/13825585.2010. 517826, pp. 1-18. (NIH-PA Author Manuscript).

Immanuel Babu Henry Samuel et al., "Compensatory Neural Responses to Cognitive Fatigue in Young and Older Adults", Frontiers in Neural Circuits, Published: Feb. 2019, vol. 13, Article 12, pp. 1-12 (Original Research, doi: 10.3389/fncir.2019.00012).

* cited by examiner

20

MEDICATION ENHANCEMENT SYSTEMS AND METHODS FOR COGNITIVE BENEFIT

CROSS-REFERENCE TO RELATED APPLICATION

This application claims priority to U.S. Provisional Patent Application No. 62/817,962, filed on Mar. 13, 2019, the entire disclosure of which is hereby expressly incorporated by reference.

GOVERNMENT RIGHTS

This invention was made with government support under Small Business Innovation Research Grant No. 1R43AG065035-01 awarded by the National Institutes of Health. The Government has certain rights in the invention.

BACKGROUND

Field of the Disclosure

The present disclosure relates to systems and methods for medication enhancement and cognitive benefit, and in particular, to systems and methods for providing computer-generated cognitive therapy games and enhancements to cognitive medication.

Related Art

A 2013 report by the Alzheimer's Association showed that over 5 Million Americans suffer from dementia and its more severe variant called Alzheimer's disease ("AD"). According to the Alzheimer's Association, by 2019 the number of afflicted Americans had grown by about 40%, to 7.1 Million. AD is considered an irreversible neurodegenerative disorder.

Pharmacological approaches are frequently prescribed to treat AD, however, they are not always effective in treating cognitive impairments. Studies have shown that AD related cognitive impairments can affect decision making and problem solving (collectively called executive functions), memory, ability to focus, and quality of life. One study, which involved a review of 18 clinical studies on 802 patients, found that non-pharmacological approaches (physical exercise) to treating AD demonstrated benefits in the cognitive domains of memory, language, and attention in patients with AD. Studies have also found that physical activity interventions alone, or combined with other therapies, were effective in improving executive functions and self-reported concentration, while other studies have shown only a 0.4% success rate with pharmacological approaches, referred to herein generally as cognitive medication.

Web-based game treatment involving intellectual activities in the home is a newer form of non-pharmacological intervention which has been shown to delay the onset of dementia in elderly individuals. Integrative virtual rehabilitation is a rehabilitation method that uses virtual reality to simultaneously target the body, mind, and patient well-being. In some instances, integrative virtual rehabilitation can combine two non-pharmacological approaches that were found to benefit cognition for the elderly, e.g., physical activity and cognitive training. Furthermore, virtual rehabilitation game therapy has been found to be adaptable, highly motivating, and facilitate more intensive and integrative cognitive training than conventional approaches.

The BrightBrainer Rehabilitation System is a commercially available system and Class I medical device developed by Bright Cloud International Corp., which treats patients with deficits in attention, memory, executive functions, and other cognitive and neuromuscular conditions. It does so through custom therapeutic games that adapt to the patient's needs and ability on a day-to-day basis. Embodiments of the BrightBrainer Rehabilitation System are shown and described, for example, in U.S. Pat. No. 9,724,598, issued Aug. 8, 2017, entitled "Bimanual Integrative Remote Therapy System and Method" to Burdea, the entire disclosure of which is hereby incorporated by reference. Therapeutic games, such as those implemented by the BrightBrainer Rehabilitation System and described in U.S. Pat. No. 9,724,598, were shown to improve the focus and independence of severely impaired patients, e.g., patients with no working memory, no independence, flat emotional affect, within six (6) weeks (e.g., 18 sessions). U.S. Pat. No. 9,724,598 also discloses the use of certain food supplements for improved cognitive outcomes for patients playing cognitive bimanual games and the use of extra oxygen during therapeutic game play.

Studies have also found that such therapeutic games can improve executive function and reduce depression in impaired patients. Therapeutic games have also been found to benefit patients with cognitive impairments in eight (8) weeks (e.g., 16 sessions). Some benefits include improvement in language and reduction in mild cognitive impairments ("MCI"). For example, at least one patient, who initially presented with MCI, tested normal after eight (8) weeks of treatment using therapeutic games and maintained normal cognition after eight (8) weeks without therapeutic games. Additionally, in at least one instance an impaired male with Primary Progressive Aphasia started reading again and had improved behavior after BrightBrainer Rehabilitation System sessions.

Moreover, participants and therapists of a feasibility trial that targeted 21 individuals suffering with chronic post traumatic brain injury and/or stroke who underwent 18 BrightBrainer Rehabilitation System sessions have reported moderate to high levels of satisfaction with the system, and therapy was found to trend towards clinical effectiveness in Automated Neuropsychological Assessment Metrics.

Bright Cloud International Corp. also showed the feasibility of integrative VR-based rehabilitation for individuals chronic post-stroke living at home, e.g., through the use of a BrightBrainer Rehabilitation System. FIG. 1A is a diagram showing hardware components of the BrightBrainer Rehabilitation System, indicated at 10. As shown, the system 10 includes a movable platform 11, a medical grade computer 12, an enclosure 13, a large display 14, a tracking means 15, a multitude of game controllers 16, held by the patient 17 and a power supply 18. The BrightBrainer Rehabilitation System 10 also incorporates a Head Mounted Display ("HMD") 19 placed in the enclosure 13 and wired to the computer 12.

The system 10 can also include one or more game controllers 16, such as the commercially available HTC VIVE controllers. FIG. 1B is a diagram showing a BrightBrainer Grasp therapeutic game controller 20, which can also be used in connection with the system 10. Therapeutic game controller 20 is described in detail in U.S. Patent Application Pub. No. 2017/0361217, published Dec. 21, 2017, entitled "Bimanual Integrative Virtual Rehabilitation System and Methods," to Burdea et al., the entire disclosure of which is hereby expressly incorporated by reference. Therapeutic game controller 20 is also described in Burdea et al., "Novel Therapeutic Game Controller for Telerehabilitation of Spastic Hands: Two Case Studies," *Proc.* 13$^{th}$

*Int. Conf. Virtual Rehabilitation*, Tel Aviv Israel, July 2019, pp. 8, the entire disclosure of which is hereby expressly incorporated herein by reference.

Telerehabilitation intervention has been found to improve motor function, improve cognition, improve language, improve cognitive metrics, and decrease depression in patients suffering chronic impairments after stroke.

Computer games have also been used to diagnose dementia, as described in U.S. Patent Application Pub. No. 2016/0038075, published Feb. 11, 2016, entitled "Bimanual Computer Games System for Dementia Screening," to Burdea et al., the entire disclosure of which is hereby expressly incorporated by reference. The use of computer games to diagnose dementia is also detailed in House et al., "A serious-gaming alternative to pen-and-paper cognitive scoring—a pilot study," *Int. Conference on Disability and Virtual Reality Technology,* Sweden, 2014, the entire disclosure of which is hereby expressly incorporated herein by reference. The BrightScreener Rehabilitation System was tested as a screening system for individuals with dementia, including Alzheimer's disease. In this regard, a feasibility study was undertaken to determine if the BrightScreener Rehabilitation System was able to differentiate levels of cognitive impairment based on game performance alone, as well as to evaluate technology acceptance by a target population with dementia. It was found that BrightScreener Rehabilitation System implementing therapeutic games can be used as a digital technique to stratify levels of cognitive impairment. These results demonstrate that computerized systems using bimanual game interfaces are one alternative to conventional standardized scoring for Mild Cognitive Impairment and Dementia.

Web-based software applications like Elevate or Lumosity train cognition, but limit motor training to 2D uni-manual interactions. As such, they are unable to provide the needed physical exercise component shown to benefit early AD. Other integrative products such as Intendu or Jintronix utilize vision to track arm movements, but are unsuitable to track fingers. This limits the complexity of the training tasks. Furthermore, they rely on the Kinect system, a tracking device by Microsoft that is no longer made. Further still, none of these products incorporate a biosensor system to measure cognitive engagement, or use cognitive load and/or cognitive engagement as inputs in therapy shaping. None of these systems teach using, dosing, or monitoring cognitive medication use in conjunction with therapeutic games.

Additionally, combined (or integrative) remote rehabilitation systems are known in the art, such as the system described in U.S. Pat. No. 9,028,258, entitled "Combined Cognitive and Physical Therapy" to Burdea, the entire disclosure of which is hereby incorporated by reference.

Systems that use integrative virtual rehabilitation for individuals with dementia, Alzheimer's Disease, or other cognitive diseases, and are provided in the home for the benefit of patients and caregivers are needed. Additionally, systems and methods that leverage both cognitive training games and traditional medications for treating cognitive impairment, in order to combat Alzheimer's disease and other cognitive diseases are needed and have not yet been developed.

SUMMARY

In accordance with some aspects of the present disclosure, a system for measuring cognitive engagement using a combination of cognitive therapy game performance and physiological measurement data from a biosensor-integrated all-in-one head mounted display worn by a patient is provided. The biosensors can be cognitive engagement detection devices, such as, for example, skin temperature sensors, skin conductance measurement sensors, a blood oxygenation measurement system, an eye blinking detection system, an eye gaze detection system, and a head movement detection system. This data can be used by the system of the present disclosure to adapt one or more game parameters to the patient's momentary cognitive engagement response or degree of cognitive fatigue. For example, the type, intensity and challenge of the games can be modulated based on this information. The average difficulty of one or more games during a therapy session can also be monitored by the system of the present disclosure. As such, the system can adjust game session difficulty level based on a combination of the patient's performance and an index of cognitive load and cognitive engagement.

In some aspects, the system can determine a level of cognitive engagement of the patient based on the data generated by the cognitive engagement detection device, determine performance of the patient interacting with the therapeutic games based on information received from the game controllers, and determine cognitive improvement of the patient based on the cognitive engagement and the performance of the patient.

The system of the present disclosure can also be used over long durations of time in the home, as cognitive maintenance, which has been shown to reduce the incidence of dementia in aging populations, or reduce dementia severity after diagnosis. Thus, according to some aspects of the present disclosure, an in-home cognitive maintenance system is provided, which can be supplemented by other techniques used in brain wellness. For example, cognitive maintenance games generated by the system of the present disclosure can be used in isolation, or in combination with such techniques as outdoors physical exercising, reading books, learning a foreign language, socializing, yoga, or eating brain-stimulating foods.

According to some aspects of the present disclosure, the system can determine a galvanic response trend from a previous game played by a patient and an artificial intelligence (AI) algorithm can analyze the galvanic response trend to adjust one or more environmental game parameters of the next game. Thus, in a game-based rehabilitation session, when multiple games are played, the system can offer an optimized and winnable game setting for everyone, regardless of individual performance level.

According to some aspects of the present disclosure, the system can combine intense, remotely monitored cognitive training games and medication for cognitive diseases, to increase effectiveness of the cognitive medication. According to aspects of the present disclosure, the system can combine cognitive medication with therapeutic game scenes played by the patient to reduce rate of cognitive degradation and the cost of healthcare. According to aspects of the present disclosure, the type and dosage of the cognitive medication can be modified based on a cognitive state that is reported by a home-based system utilizing artificial intelligence software.

BRIEF DESCRIPTION OF THE DRAWINGS

The foregoing features of the disclosure will be apparent from the following Detailed Description, taken in connection with the accompanying drawings, in which.

DETAILED DESCRIPTION

The present disclosure relates to systems and methods of combining intense, remotely monitored cognitive training games and customary medication for cognitive diseases, such as early Alzheimer's disease ("AD"). The integration of computerized cognitive training games with the customary medication is done to increase the response and effectiveness of the cognitive medication. While the description below is directed towards one or more patients 17 (see FIG. 2) with AD, some systems and methods of the present disclosure can be used by patients 17 with other medical conditions. For example, other patients that can benefit from such a combined therapy and therapeutic gaming in telerehabilitation include, but are not limited to, those who have survived a stroke, those who have sustained a Traumatic Brain Injury, or those who underwent chemotherapy and suffer from lasting cognitive impairments. Some, or all, of these patient groups can also take cognitive medications.

Figure 2:
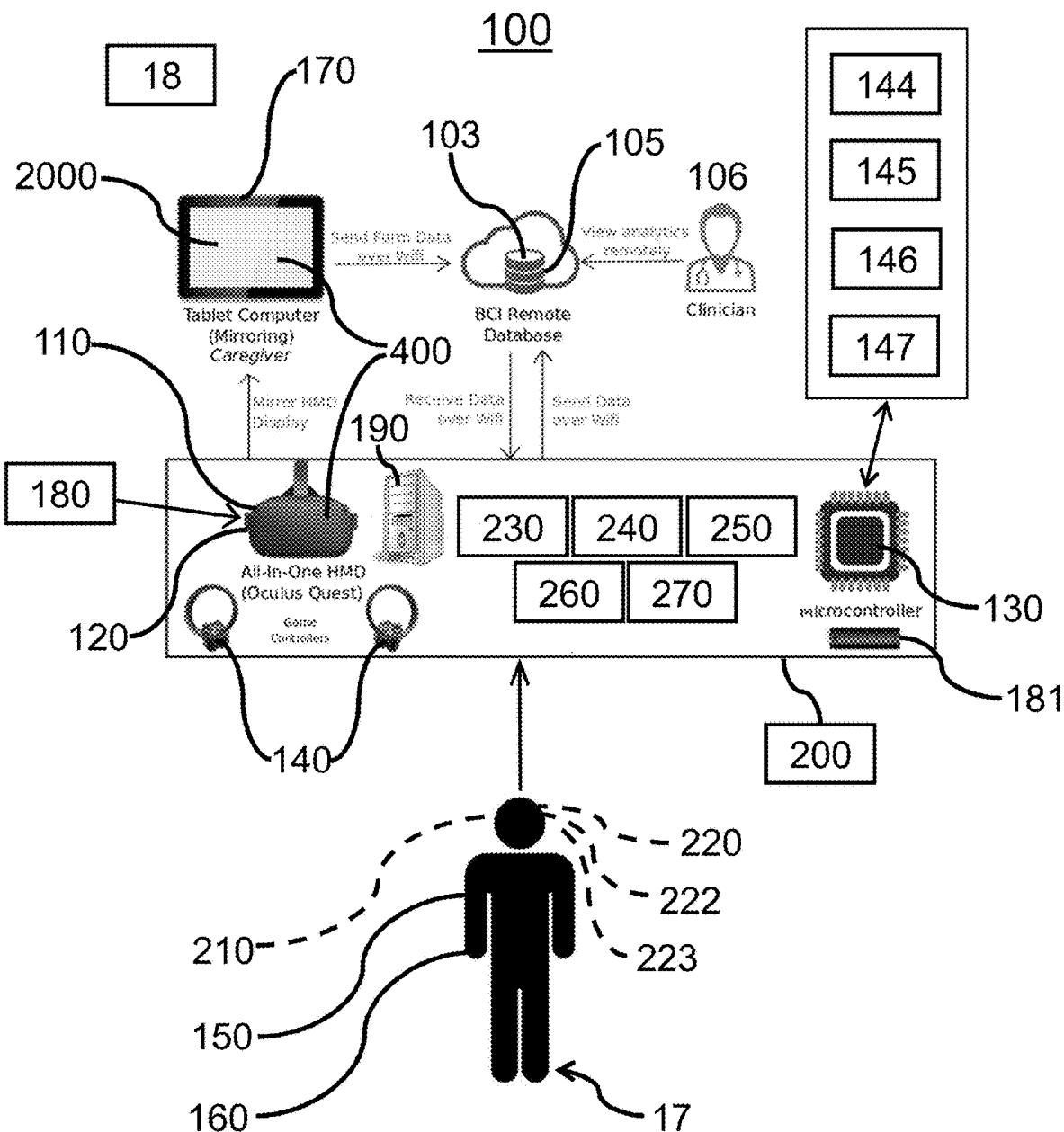
FIG. 2 is a diagram illustrating hardware and software components of a cognitive game therapy system according to the present disclosure.

FIG. 2 is a diagram illustrating hardware and software components of a system 100 of the present disclosure for combined cognitive medication 144 and therapeutic games 145 training for patients 17, patient 17 having cognitive impairments (such as Alzheimer's disease). A method of cognitive intervention is coupled with a measurement of associated cognitive engagement 210. The system 100 and method can be used at home 102 by the patient 17, or can be utilized in other settings, such as hospitals, assistive care facilities, or the like. Data 103 associated with the patient 17 can be stored on a remote database 105. A remote clinician 106 can access the database 105 to determine the patient's 17 cognitive engagement 210, cognitive fatigue 220, cognitive improvement 222, or a combination thereof. The remote database 105 can receive other the patient 17 data, and the remote clinician 106 can access such other data. The remote clinician 106 can access data from a plurality of patients 17, and a plurality of clinicians 106 may access data from a plurality of patients 17.

As shown in FIG. 2, the system 100 can include a biosensor module 110, an all-in-one Head Mounted Display (HMD) 120, game controllers 140, and cognitive medication 144. The cognitive medication 144 can be prescribed by remote clinician 106, and taken by the patient 17 as customary treatment for cognitive diseases 223. It is understood by those skilled in the art that the game controllers 140 can measure arm 150 movements during game play in response to cognitive training scenes 400, which can be, for example, cognitive games or game scenes 400. According to some aspects of the present disclosure, the game scenes 400 can be presented on the HMD 120 and replicated on a tablet 170. Replicating the cognitive training scenes 400 on the tablet 170 allows a caregiver 18 of the patient 17 to monitor the patient's 17 actions. The tablet 170 can also transmit the cognitive training scenes 400 to the remote clinician 106. Alternatively, or additionally, the HMD 120 can transmit the game scenes 400 to the remote clinician 106. According to some aspects of the present disclosure, the patient 17 can take off the HMD 120 and play while looking at the cognitive training scenes 400 as they are displayed on the tablet 170. The HMD 120 can also be linked to a television, computer monitor, or display via wired or wireless connection, such that the patient 17 can take off the HMD 120 and play while looking at the television, computer monitor, or display.

The all-in-one HMD 120 can be a commercially available HMD, for example, but not limited to, an all-in-one HMD sold under the brand name Oculus Quest. Computing hardware of the all-in-one HMD 120 can include a multi-core processor 130 having cores allocated to computing graphics cognitive training scenes 400, tracking game controllers 140, or the like. The all-in-one HMD 120 can be powered by a battery 181, but the life of the battery 181 (e.g., runtime) can be a limiting factor for how long the patient 17 may be immersed in cognitive training scenes 400. As such, the all-in-one HMD 120 can be plugged into, and rely on, a separate power supply 180.

Figure 1A:
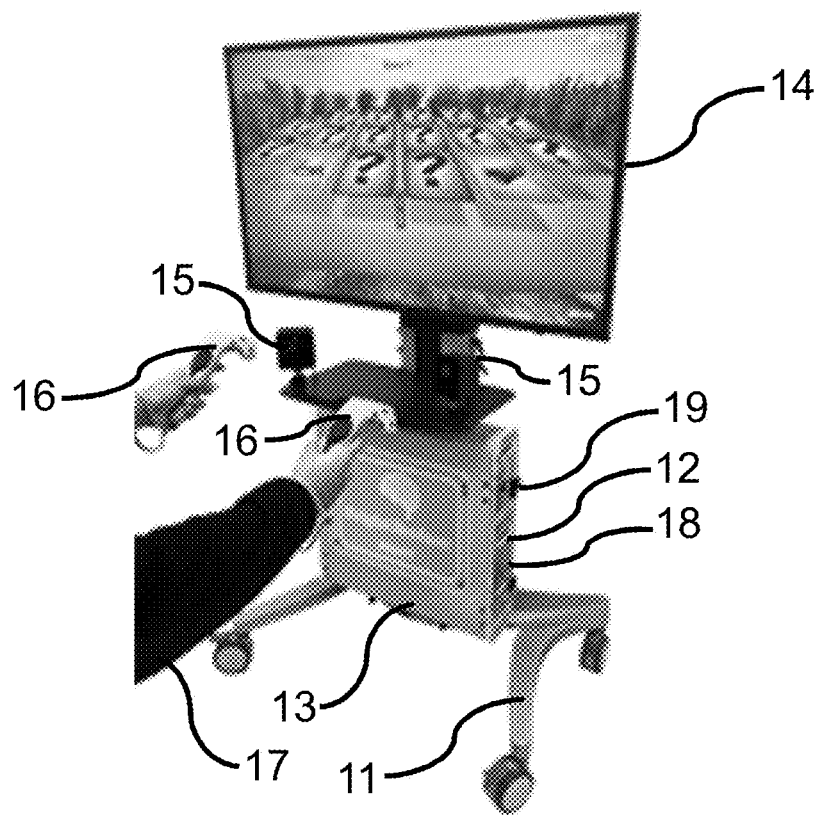
FIG. 1A is a diagram showing hardware components of a prior art virtual reality cognitive game rehabilitation system.
Figure 1B:
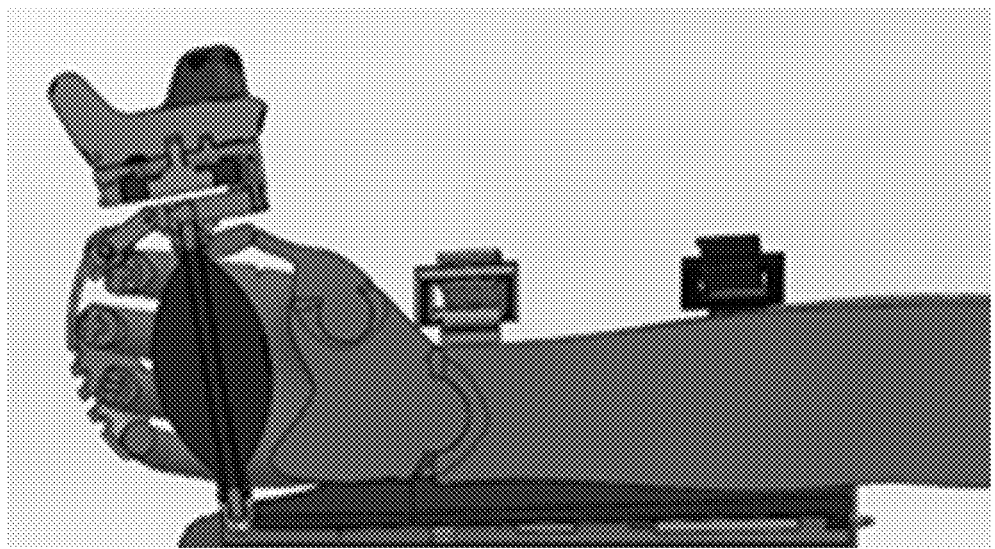
FIG. 1B is a diagram showing a game controller for a prior art cognitive game rehabilitation system.

It is understood by those skilled in the art that two game controllers 140 can be held, one in each hand 160, and the patient 17 can use the game controllers 140 to control avatars 2000 in the game cognitive training scenes 400. It is further understood, that this is only one of a multitude of possible configurations, for example, a wireless or wired HMD 120 without its own computing hardware 130 can also be used by the patient 17. In such a configuration, game cognitive training scenes 400 can be computed by a separate computer 190. The separate computer 190 can be a Personal Computer, a tablet computer, a laptop, a game console, a smart phone, or other computation elements as those known in the art.

Where the system 100 utilizes a separate computer 190, a cable can transmit game cognitive training scenes 400 to the HMD 120 for presentation to the patient 17. It is understood by those skilled in the art that a cable can be eliminated via the use of wireless transmissions between the separate computer 190 and the HMD 120. According to some aspects of the present disclosure, the separate computer 190 provides data to the HMD 120, however game cognitive training scenes 400 are created within the HMD 120. According to other aspects of the present disclosure, the separate computer 190 can utilize a large display 14, such as illustrated in FIG. 1A.

One component of the system 100 is a cognitive engagement detection device 200 for detecting cognitive engagement 210, which can include one or more individual devices. Cognitive engagement 210 has been previously understood as investment of mental effort in order to complete an independent learning task online. However, cognitive engagement 210 is understood herein as mental effort of the patient 17 who is learning to interact with game cognitive training scenes 400 and succeeds in performing related gaming tasks 146. The cognitive engagement detection device 200 for detecting cognitive engagement 210 may include one or a plurality of skin temperature sensors 230, skin conductance measurement sensors 240, blood oxygenation measurement system 250, blinking detection system 260, head movement detection system 270, or a combination thereof (see FIG. 3).

Figure 3:
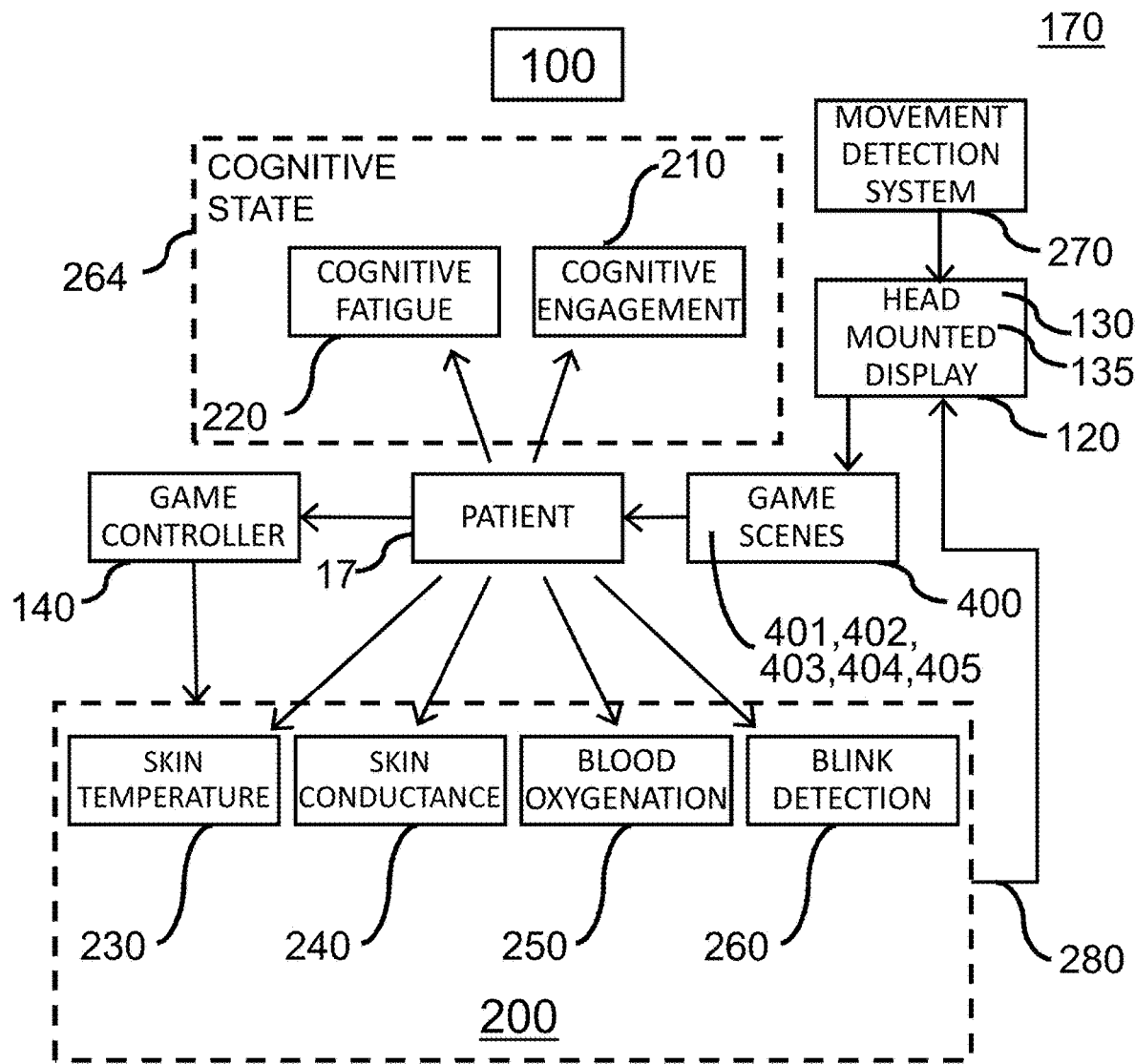
FIG. 3 is a diagram illustrating means for detecting cognitive engagement of the cognitive game therapy system of the present disclosure.

FIG. 3 is a diagram illustrating the cognitive engagement detection device 200 for detecting cognitive engagement 210 of the system 100 of the present disclosure. Artificial Intelligence software 135 can run on the all-in-one HMD 120 processor 130 or on the separate computer 190. Artificial Intelligence software 135 can receive input from one or a plurality of the sensors and systems 230, 240, 250, 260 and 270, and cam receive input from the game controllers 140. The systems 230, 240, 250, 260, 270 and game controllers 140 can be in contact with, or actuated by, the patient 17. The artificial intelligence software 135 can accordingly adjust game difficulty 401, game duration 402, game interaction modality 403, game cognitive cues 404, and available game selection 405. In doing so, Artificial Intelligence software 135 can maximize cognitive engagement 210, while monitoring cognitive fatigue 220.

Head movement detection system 270 can include a tracking system of the HMD 120. The cognitive engagement detection device 200 for measuring cognitive engagement 210 can include any of the sensors or system 230, 240, 250, 260, 270, or a combination thereof. Additionally, the cognitive engagement detection device 200, singularly or collectively, can provide feedback 280 to the HMD 120 processor 130, or the separate computer 190, on measure(s) obtained from the patient 17. The HMD 120 processor 130 or separate computer 190 can then adjust the game cognitive training scenes 400 accordingly.

Figure 4:
FIG. 4 is a front view of a head mounted display device according to the present disclosure.

FIG. 4 is a front view of the HMD 120 of the system 100 according to the present disclosure. As shown, the HMD 120 can include straps 310 configured to keep the display 320, located inside the HMD 120, attached to the patient's 17 forehead 330. A display 320 can present game scenes 400 to the patient 17. It is further understood by those skilled in the art that the HMD 120 can include a head movement detection system 270 configured to determine the patient's 17 head movement and adjust game cognitive training scenes 400 accordingly. The head movement detection system 270 can include one or a plurality of cameras 271. The cameras 271 can be infrared cameras and can also be used to measure movements of the game controllers 140 held by the patient 17.

Figure 5:
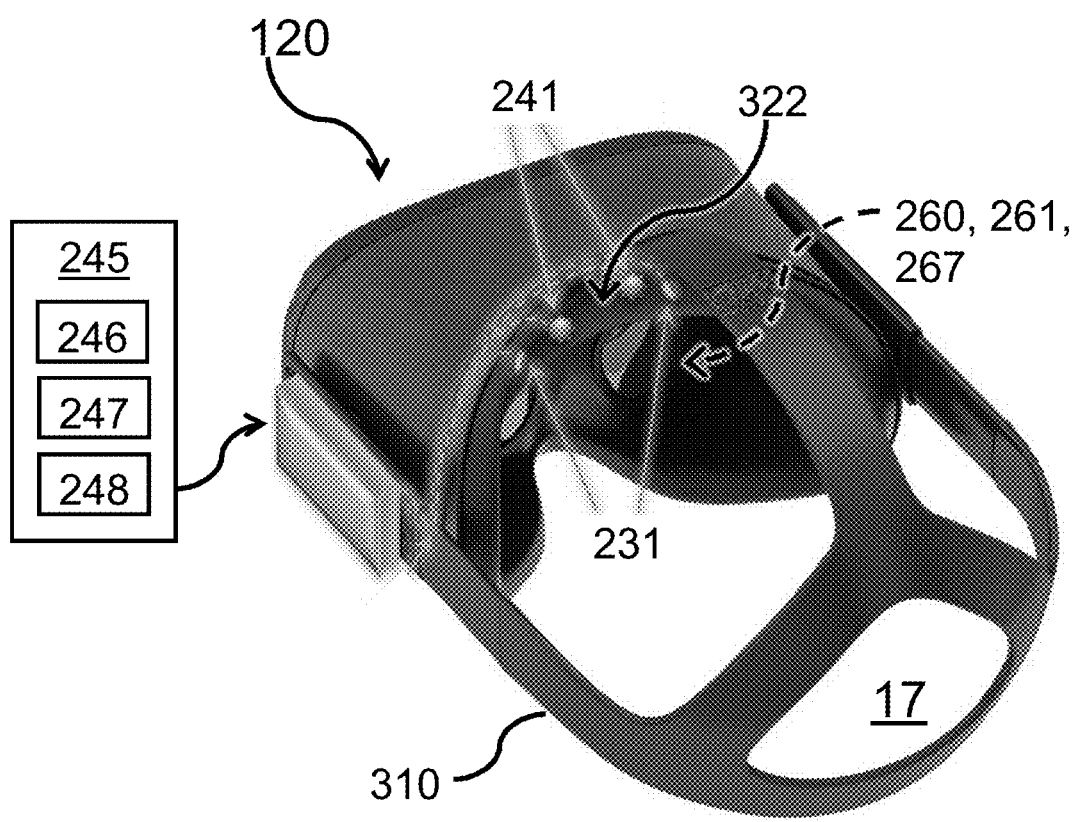
FIG. 5 is a perspective view of the head mounted display device of FIG. 4 according to the present disclosure.

FIG. 5 is a perspective view of an HMD 120 of the system 100 according to the present disclosure. The cognitive engagement detection device 200 for measuring cognitive engagement can be incorporated into a compliant surface 233 of the HMD 120 that can be placed on, and around, the forehead area 330 of the patient 17. The cognitive engagement detection device 200 for determining cognitive engagement 210 can be formed from a plurality of galvanic skin response sensors 231, and the means 230 can be further formed from a plurality of temperature sensors 241, such as those known in the art. As shown in FIG. 5, galvanic skin response sensors 231 and temperature sensors 241 can be placed side by side, and in an alternating fashion on the compliant area 322 of the HMD 120.

The HMD 120 can be configured such that the patient's 17 forehead 330 contacts the galvanic skin response sensors 231 and temperature sensors 241 when the patient 17 wears the HMD 120. In this case, such contact can be due to elasticity and shape of the HMD 120 and straps 310, as well as placement of the galvanic skin response sensors 231 and temperature sensors 241 in the HMD 120 compliant area 322. For example, the HMD 120 compliant area 322 can press the galvanic skin response sensors 231 and temperature sensors 241 against the forehead area 330. Circuitry of the galvanic skin response sensors 231 and temperature sensors 241 can be in communication with (e.g., wired to) the controller module 245, which can be located on an exterior surface of the HMD 120. The controller module 245 can include a power means 246 to provide electricity needed by circuitry of the galvanic skin response sensors 231 and temperature sensors 241. Additionally, the controller module 245 can include a processor 247 and a communication means 248. Such communication means 248 can be used to send data from circuitry of cognitive engagement detection device 200 to the microprocessor 130, so to affect one or more changes in game cognitive training scenes 400.

The HMD 120 can also include an eye blinking detection system 260 and an eye gaze detection system 261. The blinking detection system 260 can be in the form of specialized glasses 267. The glasses 267 can also include the eye gaze detection system 261. Both blink rate and eye gaze are known to correlate to cognitive state 264 of a patient 17. The glasses 267 are not necessarily shaped similar to standard glasses (e.g., eyeglasses), and do not necessarily contain lenses, as exemplified by Pupil Lab's Core eye tracking headset. According to some aspects of the present disclosure, the eye blinking detection system 260 and eye gaze detection system 261 can be mounted directly within the HMD 120, without the use of the specialized glasses 267.

Figure 6:
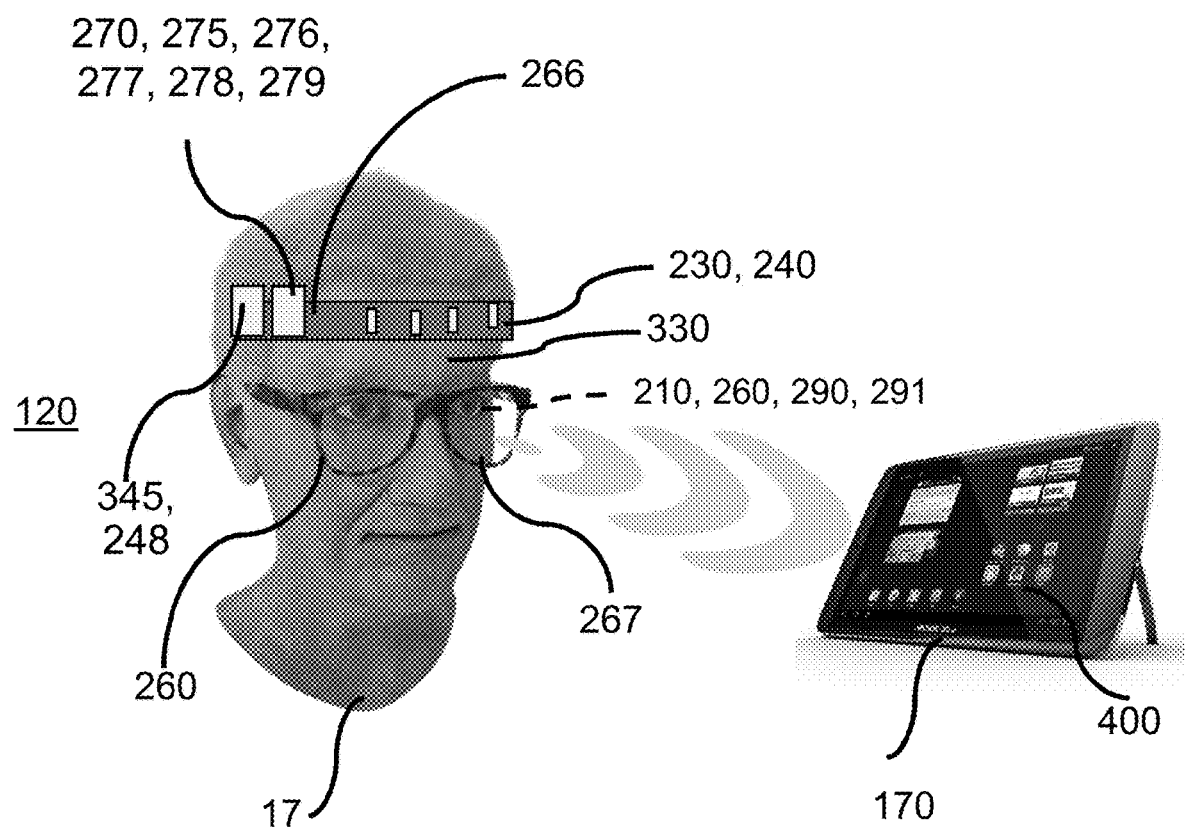
FIG. 6 is a diagram illustrating hardware and software components of another cognitive engagement detection system according to the present disclosure.

FIG. 6 shows a headband 266 and specialized glasses 267 of the system 100, according to the present disclosure, positioned on the patient 17. If the patient 17 does not wear the HMD 120, as discussed in connection with FIGS. 4 and 5, the means 230, 240 can be provided on the headband 266. As shown in FIG. 6, the headband 266 can be oriented such that the means 230, 240 are pressed against the forehead area 330 of the patient 17. The headband 266 can also incorporate a controller module 345. In the configuration of FIG. 6, the patient 17 can observe game cognitive training scenes 400 on the tablet 170 while wearing the specialized glasses 267. As discussed herein, the glasses 267 can include a blinking detection system 260 and an eye gaze detection system 261. For example, the glasses 267 can be those available commercially from Pupil Labs. The headband 266 can also include a wireless communication means 248 which transmits data from the means 230, 240, 260 to the tablet 170 to affect content of the game cognitive training scenes 400. In the configuration of FIG. 6, the game scene 400 can always be viewed by the patient 17. The head movement detection system 270 can also be incorporated in the headband 266 to determine when the patient 17 looks away from the game cognitive training scene 400. According to some aspects of the present disclosure, the head movement detection system 270 can include a six (or more)-degree of freedom tracker 275, inertia sensors 276, ultrasonic sensors 277, vision cameras 278, magnetic trackers 279, other technologies for tracking head movement known in the art, or a combination thereof.

Eye gaze 290 and spontaneous blink rates 291 are complementary measurements of cognitive engagement 210 of the patient 17. According to some aspects of the present disclosure, one or more additional physiologic sensing elements can be included in the system 100 that will have complemental, but distinct measurement capabilities for the purposes described herein. As described herein, one or more custom therapeutic games 145 can be played with one, or both, arms 150 and one or both controllers 140, so to also improve upper body motor function.

Figure 7A:
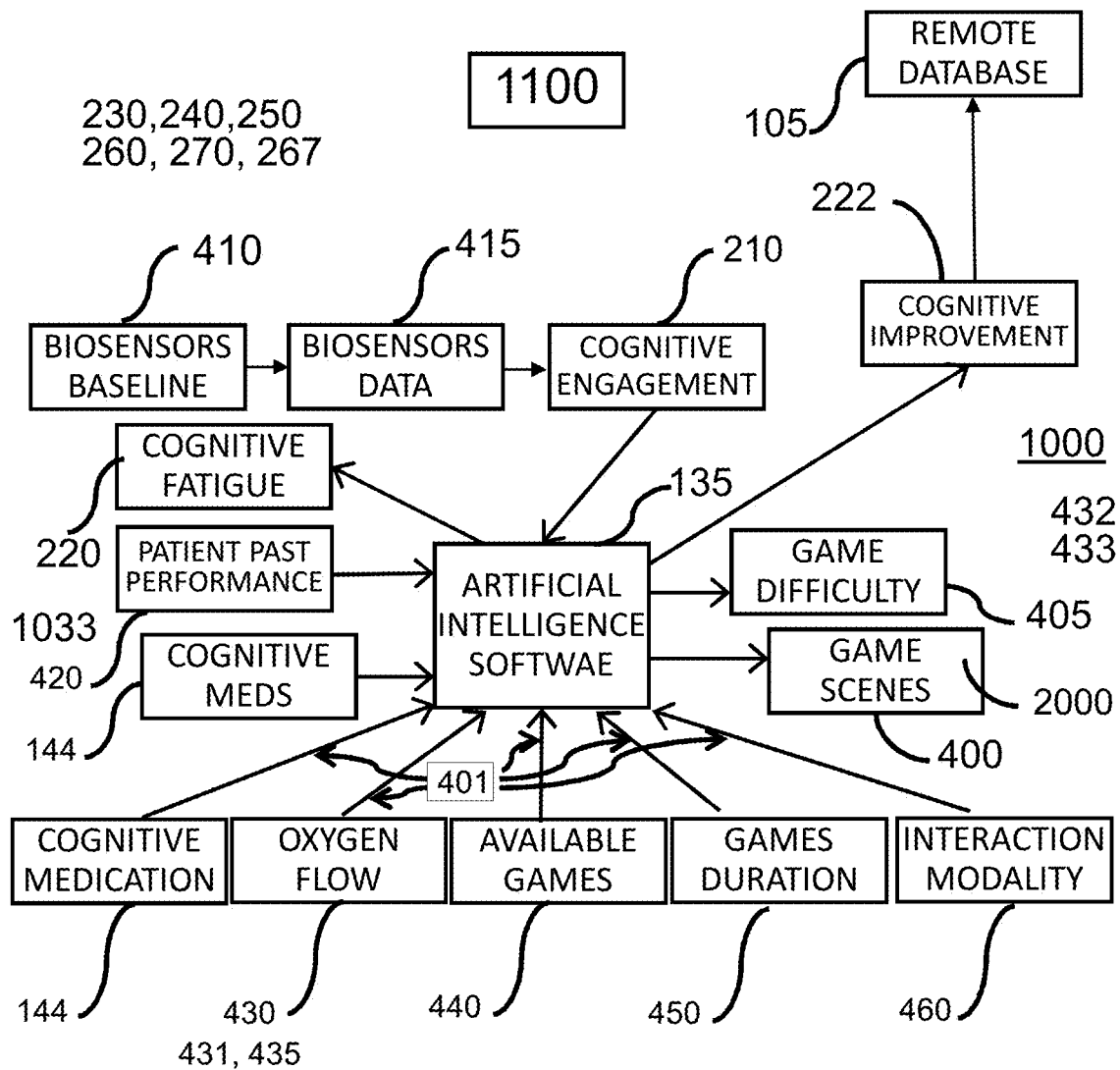
FIG. 7A is a diagram illustrating a game scene customization system according to the present disclosure.
Figure 7B:
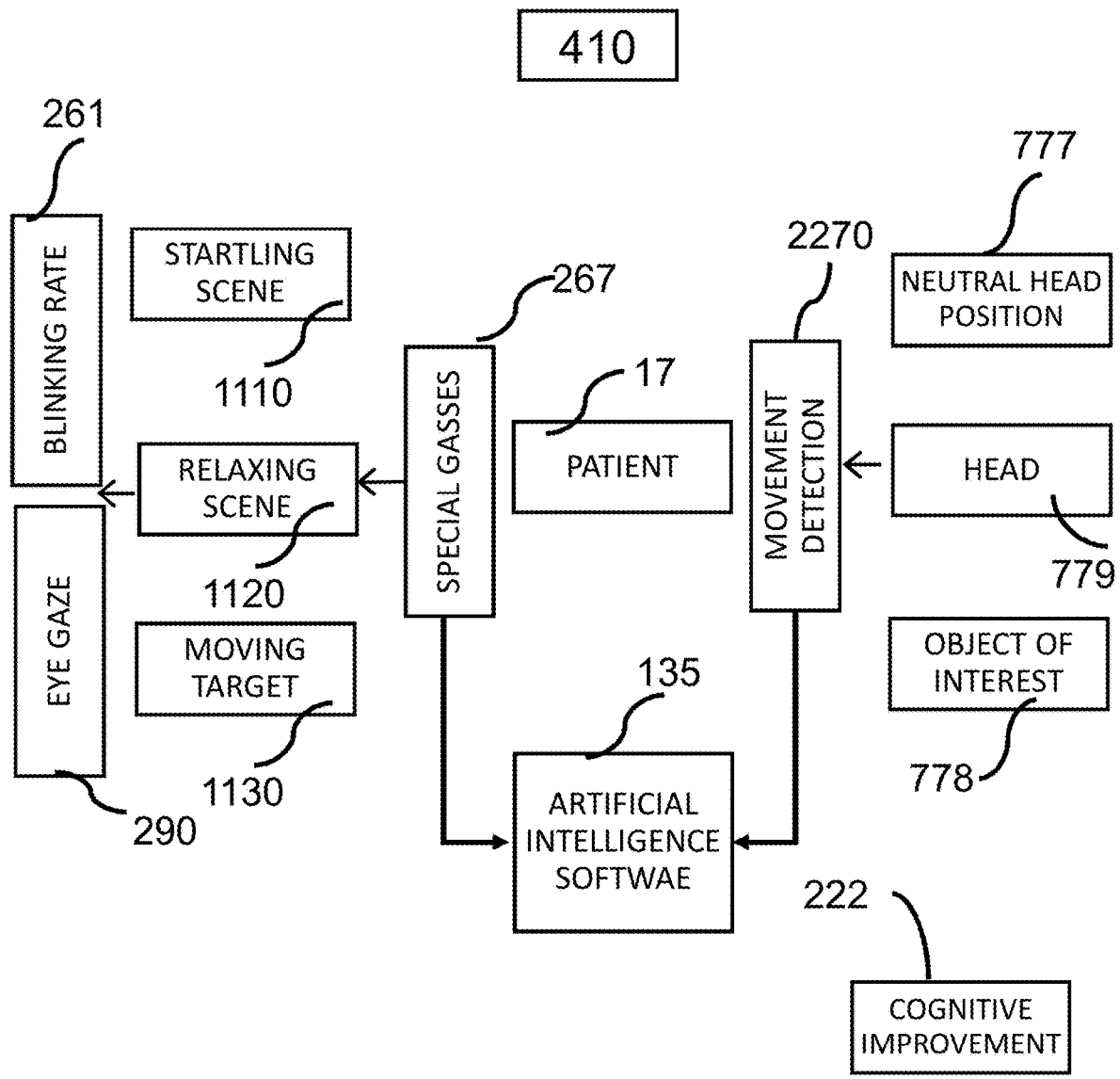
FIG. 7B is a diagram illustrating aspects of establishing a bio sensor baseline according to the present disclosure.
Figure 7C:
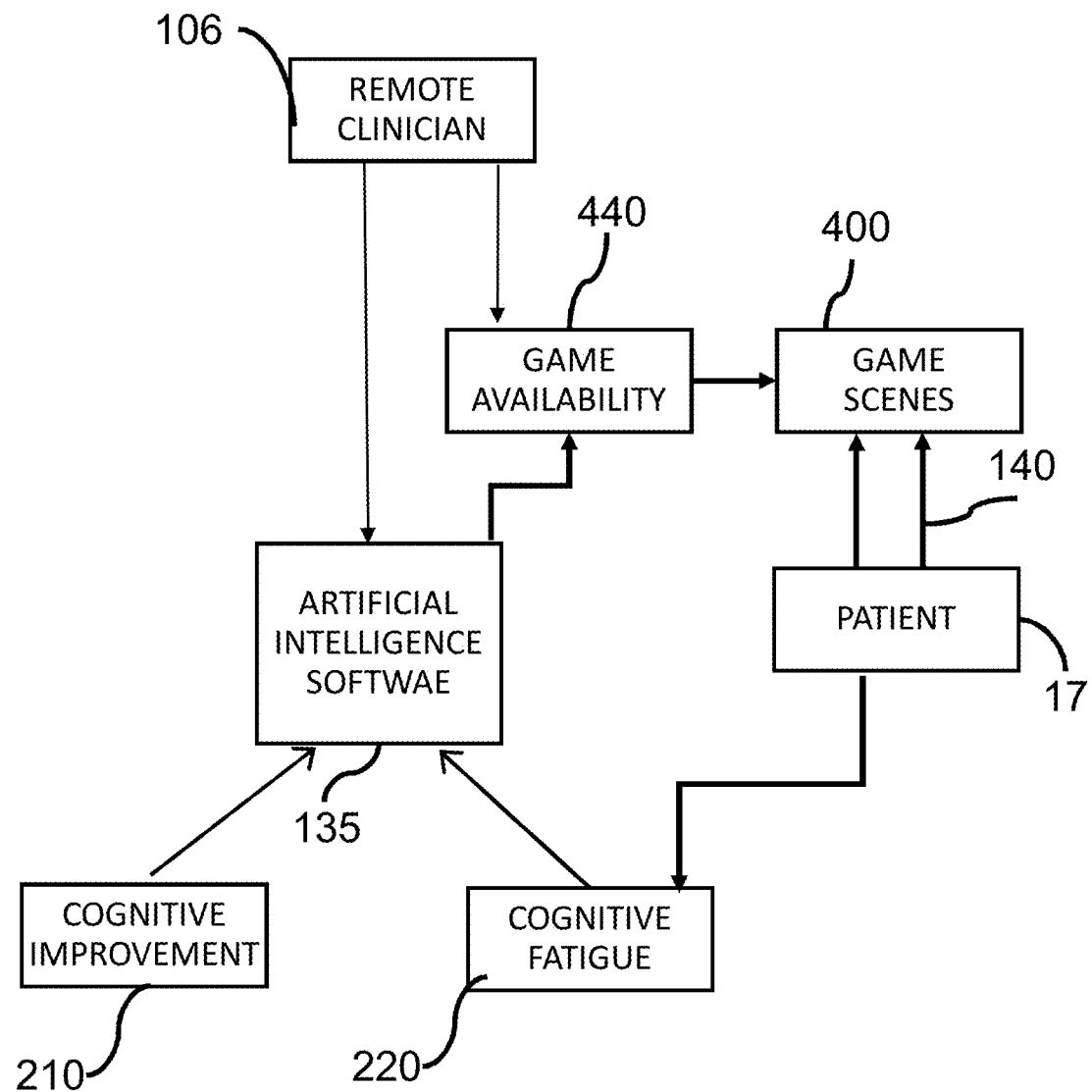
FIG. 7C is a diagram illustrating a game scene selection system according to the present disclosure.

FIGS. 7A-C illustrate systems and methods for measuring cognitive improvement and transmitting results to a remote database. Specifically, FIG. 7A is a diagram illustrating a customization system 1100 for a game-based therapy session 1000, according to the present disclosure. As shown, a multitude of game scenes 400, when played by the patient 17, form a therapy session 1000. A session customization system 1100 is provided that allows game difficulty 405 and game duration 450 of the game-based therapy session 1000 to be set. The session customization system 1100 can include an Artificial Intelligence software 135, which sets the game scenes 400 based on a plurality of inputs 401. The inputs 401 to the Artificial Intelligence software 135 can include, but are not limited to, patient 17 past performance 420 when playing game scenes 400, cognitive medication 144 taken by the patient 17, whether the patient 17 is on oxygen flow 430 (or not), availability 440 of game scenes 400 to be played by the patient 17, duration 450 of game scenes 400, difficulty 405 of game scenes 400, interaction modality 460 used to play game scenes 400, and cognitive engagement 210 of the patient 17 when playing game cognitive training scenes 400.

Those skilled in the art will understand that sufficient brain oxygenation 431 is needed for proper cognitive functioning 432. For example, U.S. Pat. No. 9,724,598, entitled "Bimanual Integrative Virtual Rehabilitation Systems and Methods" to Burdea, the entire disclosure of which is hereby incorporated by reference, teaches that extra oxygen meant to help neural activity by improving brain oxygenation is fed to a patient from an oxygen tank while the patient manipulates game avatars.

Biosensors baseline 410 can be used to interpret biosensor data 415 when deciding level of cognitive engagement 210. Biosensor data 415 can be generated by the blinking detection system 260, and the head movement 269 detection system 270. Any number of skin temperature sensors 230, skin conductance circuitry 240, blood oxygenation sensor 250, or combination thereof can also contribute to biosensor data 415. Valid interpretation of biosensor data 415 can be based on the biosensor baseline 410 for each of above mentioned biosensors. For example, the blinking detection system 260 will provide a blinking rate 261.

FIG. 7B is a diagram illustrating aspects of establishing the biosensor baseline 410, according to the present disclosure. As illustrated in FIG. 7B, while establishing the biosensor baseline 410, the blinking rate 261 of the patient 17 is measured before the start of the game therapy session 1000. Methods of measuring blinking rate 261 are those discussed herein, such as using the glasses 267, for example, Pupil Lab's Core headset, previously described. Special scenes (such as startling scenes 1110, or relaxing scenes 1120) can be played to determine blink rate 261 of the patient 17. Target objects 1130 in focusing scenes can be played to determine speed of eye gaze 290 adjustment to follow a moving object 1130 or lack thereof. Other methods can be used to measure the patient's 17 eye gaze 290 and blink rate 261, before interacting with game scenes 400 during the session 1000.

Similarly, head movement data 269 can be obtained during biosensor baseline 410, to determine how much movement a head has from a neutral position 777. For example, the patient 17 can be presented with an object of interest 778 to look at, which does not normally require head turning. If the patient 17 constantly moves their head 779 to look away from the object of interest 778, it is indicative of lack of cognitive engagement 210. Other methods can be used for determining biosensor baselines 410 and methods described herein are only examples of what is possible and what is needed by the Artificial Intelligence software 135 to determine changes from baseline 410 during the session 1000. Following biosensors baseline 410, the patient 17 using the system 100 (see FIG. 2 above), can interact with one or a plurality of game scenes 400, using one or both of the game controllers 140. The game cognitive training scenes 400 can be integrative, such that the patient 17 will need to solve cognitively demanding problems 1033, while repeatedly reaching out with one or both game controllers 140. While doing so, patient's 17 hand 160 movements can be tracked, for example, wirelessly by all-in-one HMD 120.

During each session 1000 Artificial Intelligence software 135 can track the patient 17 past performance 420 when interacting with any of a plurality of game scenes 400. The patient 17 past performance 420 can be understood to mean past error rates, past game scores, past game difficulty level 405 and game duration 450, and other such graphics scene 400-derived variables. Past performance 420 when tracked over a sequence of sessions 1000 can allow Artificial Intelligence software 135 to determine if cognitive improvement 222 in the patient 17 has occurred. Cognitive improvement 222 is then transmitted to the remote database 105 of the system 100 and monitored by the remote clinician 106.

FIG. 7C is a diagram illustrating game scene selection and availability for a therapy session 1000, according to the present disclosure. A plurality of different game cognitive training scenes 400 can be available at the beginning of each session 1000. For example, a number of game cognitive training scenes 400 constituting game availability 440, can be initially set by the remote clinician 106, and communicated to the artificial intelligence software 135. Game availability 440 can be initially be a subset of all available games. Subsequently, game availability 440 can be increased or decreased by the artificial intelligence software 135. The artificial intelligence software 135, according to some aspects of the present disclosure, can increase game availability 440 resulting in a larger number of different game cognitive training scenes 400 to motivate the patient 17. Increased motivation leads to increased cognitive engagement 210, and allows for longer durations of the session 1000. Conversely, the artificial intelligence software 135 can reduce the duration of the session 1000 to minimize cognitive fatigue 220.

Interaction modality 460 can relate to whether the patient 17 uses one or two game controllers 140 of system 100. It is known to those skilled in the art that divided attention is problematic for the elderly. When the patient 17 interacts with game cognitive training scenes 400 using two game controllers 140, divided attention occurs, possibly leading cognitive fatigue 220 to occur sooner. To minimize cognitive fatigue 220, the artificial intelligence software 135 can switch the game cognitive training scene 400 to a variant played by the patient 17 with a single controller 140.

The remote clinician 106 can introduce remote diagnostic sessions 1200 aiming to reassess level or cognitive impairment 1320 of the patient 17. For example, the clinician 106 can prescribe such remote diagnostic sessions 1200 periodically. Such remote diagnostic sessions 1200 can utilize the system 100 in the patient's 17 home 102. The diagnostic sessions 1200 can follow, for example, methods previously taught in U.S. Patent Application Pub. No. 2016/0038075, entitled "Bimanual Computer Games System for Dementia Screening," to Burdea et al.

The artificial intelligence software 135 can maximize cognitive improvement 222 while minimizing cognitive fatigue 220. Specifically, the artificial intelligence software 135 can detect cognitive fatigue 220 when the patient's 17 current performance 421 within the session 1000 diminishes over repeated interactions with the same game cognitive training scene 400, despite the patient's 17 maintaining cognitive engagement 210, and despite game difficulty 405 and game duration 450 being kept constant within the session 1000.

Upon detecting cognitive fatigue 220, the artificial intelligence software 135 can take remedial actions 1330. Such remedial actions 1330 to address cognitive fatigue 220 of the patient 17 can include, but are not limited to, reducing game difficulty 405, reducing game duration 450, introducing a brief rest period in session 1000, turning on oxygen flow 430, or increasing oxygen flow 430 (if oxygen flow 430 had already been turned on).

According to some aspects of the present disclosure, the all-in-one HMD 120 can have less performance graphics hardware 1340 than dedicated graphics hardware 1350 usually found in commercially available PCs, laptops, game consoles or other computing devices. Graphics cognitive training scene 400 content complexity 1360 can be reduced to maintain a high graphics refresh rate 1370. It is understood by those skilled in the art that graphics refresh rate 1370 can represent a number of images of a game scene 400 calculated by the graphics hardware 1340 every second. It is further understood that the system 100 can use graphics scenes 400 that have reduced content complexity 1380 to not overwhelm the patient 17. Reduction of graphics scene 400 content complexity 1380, regardless of game level of difficulty 405, is another method to diminish incidence of cognitive fatigue 220.

Figure 8:
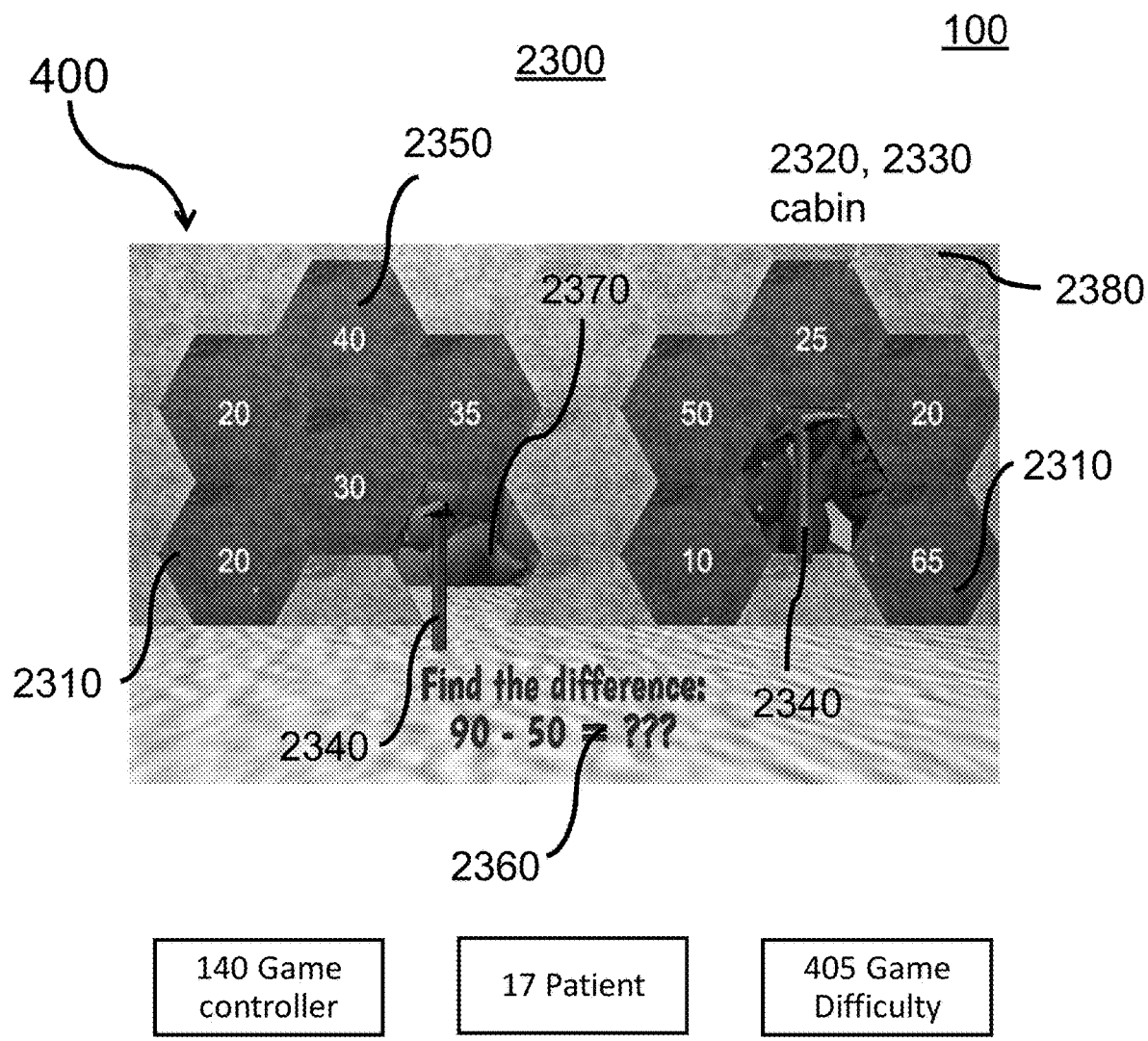
FIG. 8 is a graphical user interface generated by the system of the present disclosure, displaying a therapeutic game scene.
Figure 9:
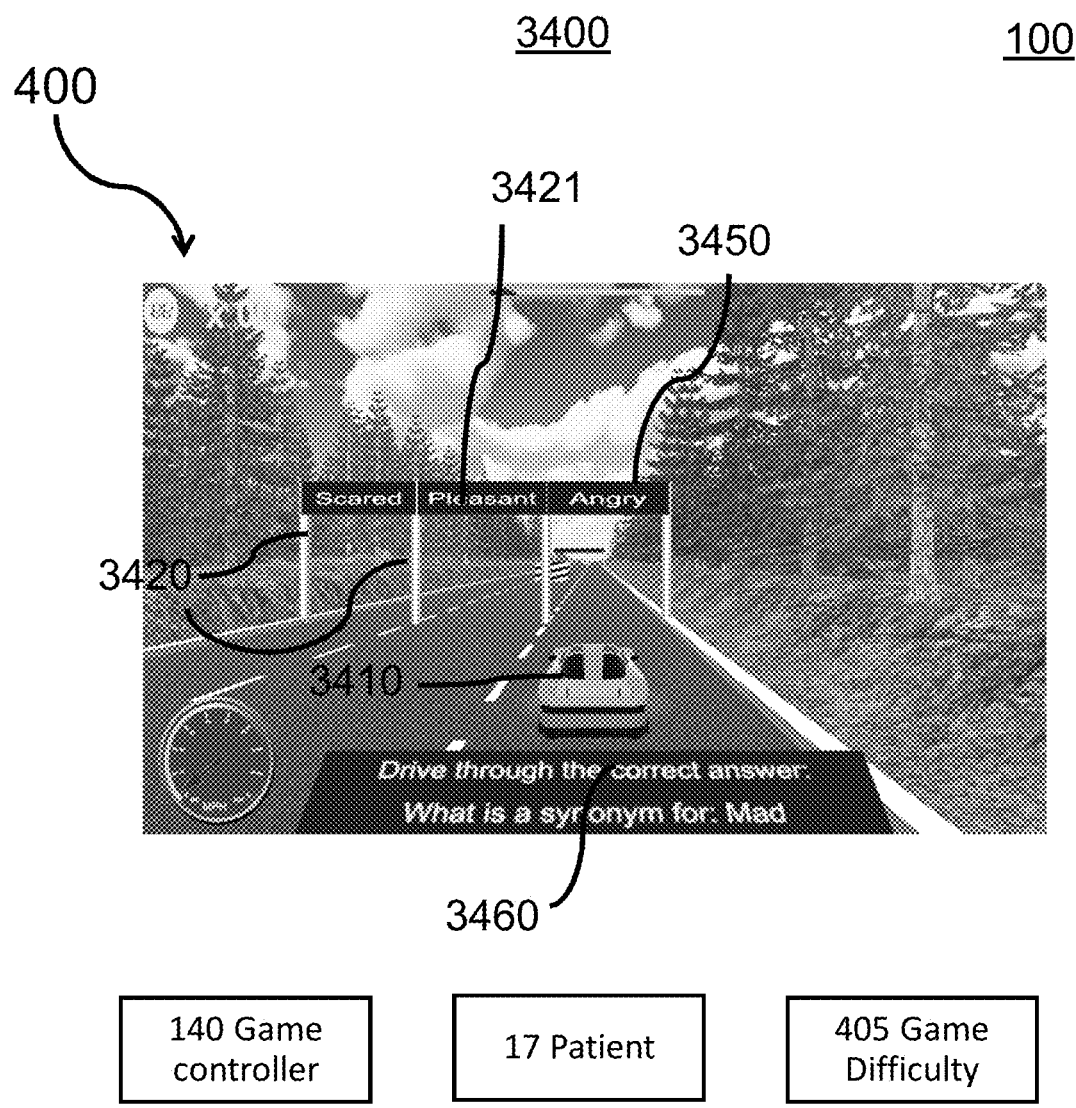
FIG. 9 is a graphical user interface generated by the system of the present disclosure, displaying another therapeutic game scene.

FIGS. 8 and 9 are graphical user interfaces generated by the system 100 of the present disclosure showing two therapeutic game scenes 400 with reduced content complexity 1380 used with the system 100. For example, FIG. 8 is a Numbers Avalanche game 2300, which asks the patient 17 to dig though ice tiles 2310 to rescue people trapped in a cabin. Each of a plurality of ice tiles 2310 can have an associated number 2315 displayed on it. The patient's 17 pickaxe avatar 2340 can successfully break ice tiles 2310 with a correct answer 2350 to arithmetic or vocabulary problem 2360 displayed on the game scene 400. As shown, the game scene 400 can ask the patient 17 to solve a subtraction equation 2360, for example, "90−50=?" which has a correct answer 2350 of "40." If the patient 17 breaks the correct answer tile 2350, thus solving the subtraction equation 2360, a hole 2370 appears in the ice wall 2380. The game 2300 can be played with one game controller or two game controllers 140. According to some aspects of the present disclosure, the two game controllers 140 control two pickaxe avatars 2340.

In the game 2300 if the patient 17 incorrectly solves the problem 2360, then ice tiles 2310 will not be broken and the hole 2370 will not appear in the ice wall 2380. After several correctly answered questions 2360, the ice wall 2380 can be cleared as the patient 17 breaks a multitude of ice tiles 2310. Higher game difficulty levels 405 can make the patient 17 break through a multitude of ice walls 2380 in order to reach the cabin and rescue the people trapped inside. Still higher levels of difficulty 405 of game 2300 can require patient 17 to complete game scene 400 in a limited time, requiring increased use of both pickaxe avatars 2340, thus increasing split attention training.

FIG. 9 is a Language Race game 3400 of the system 100. The game 3400 can ask the patient 17 to steer a car avatar 3410 through a plurality of gates 3420 using the game controllers 140. Each gate 3420 can display a word 3421 at its top. The patient 17 can be presented with a language problem 3460 on the game cognitive training scene 400. For example, the patient 17 can be asked to select a synonym to the word "Mad," from among three words 3421 displayed at the top of three adjacent respective gates 3420. The patient 17 can be asked to steer the car avatar 3410 through the gate 3420 displaying the correct answer 3450 (e.g., the word "Angry"). In so doing, the patient 17 needs to successfully split attention between driving the car avatar 3410 and solving the language problem 3460 in a limited time 3500. Due to the limited time 3500, the game 3400 trains processing speed 3510 and focus 3520. Higher game 3400 difficulty 405 can correspond to a faster car avatar 3410, which requires faster reaction time. Additionally, the patient 17 can be presented with two, four, five or more gates 3420 from which to select the correct answer gate 3450 to problem 3460.

A multitude of other game cognitive training scenes 400 are possible, and alternating different game scenes 400 is a method to maintain cognitive engagement 420. To facilitate training at home 102, a Session Scheduler can pre-load weekly games 2300, 3400 and similar sequences. According to some aspects of the present disclosure, the patient 17 can be allowed to select what game scene 400 to play next using one or a multitude of game controllers 140.

The system 100 of the present disclosure can include a Wi-Fi high-speed internet connection with a cloud server. A cloud server can store game performance and biosensor data. These data are accessible to the remote clinician 106, or to the caregiver 18. An automatic session report software can document cognitive areas trained, and other objective outcomes.

Moreover, as discussed below in connection with FIGS. 10-14, the system 100 of the present disclosure can be implemented with one or more cognitive medications, thereby improving the efficacy of both the medications and the system 100. Currently, there is no treatment to cure Alzheimer's disease, but cognitive medications that slow the progression of this disease are available. However, currently available cognitive medications have efficacy on only about 25% of patients taking such cognitive medication alone. Furthermore, such slowing of cognitive decline only lasts about six (6) months from diagnosis, after which such cognitive medication 144 loses effect.

Figure 10:
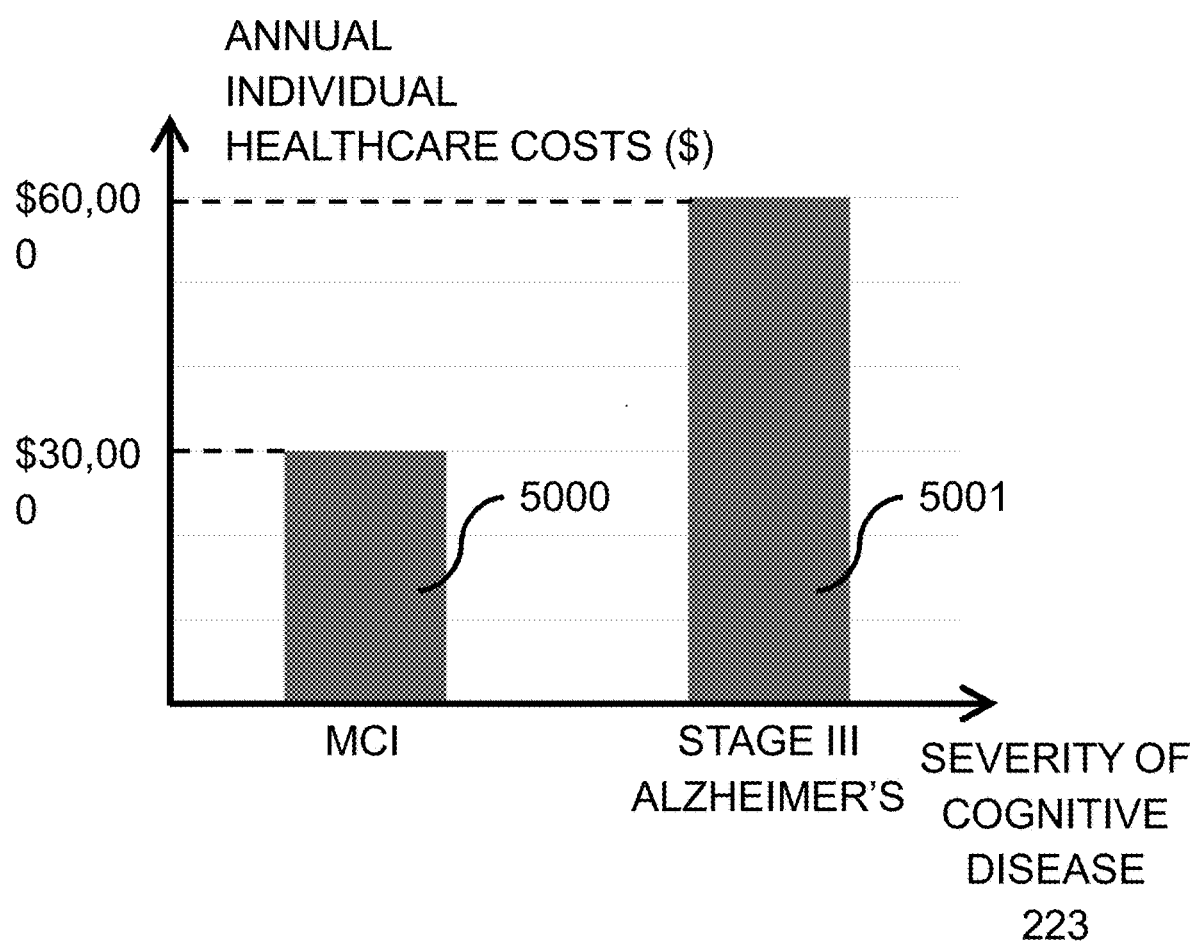
FIG. 10 is a diagram illustrating annual individual healthcare costs for patients with cognitive diseases.

Additionally, combining the system 100 with cognitive medications can drastically reduce the financial impact of treatment on patients. For example, FIG. 10 is a diagram illustrating the annual per-capita healthcare cost as a function of cognitive disease 223 severity. As illustrated in FIG. 10, there is a 200% cost differential between $30,000/year in healthcare costs for a patient 5000 who has mild cognitive impairment ("MCI") and $60,000/year in healthcare costs for a patient 5001 who has stage III (advanced) Alzheimer's Disease.

It is well understood that the cognitive disease 223 will progress over time. Furthermore, current studies estimate that patients with Alzheimer's disease have a life expectancy of 7 to 10 years if diagnosed in their early 70s, but only 3 years if they are in their 90s when diagnosed.

Early detection of mild cognitive impairment for the patient 5000 can lead to slower cognitive decline, and less cognitive disease 223 severity later in life if a plurality of treatments are prescribed. Such plurality of treatments to slow cognitive decline can include one or more of cognitive medication 144, socializing, yoga, cognitive boosting food supplements, and physical exercise. System 100, when implemented with any of the plurality of treatments enumerated, further reduces the cognitive disease 223 severity over time.

Figure 11:
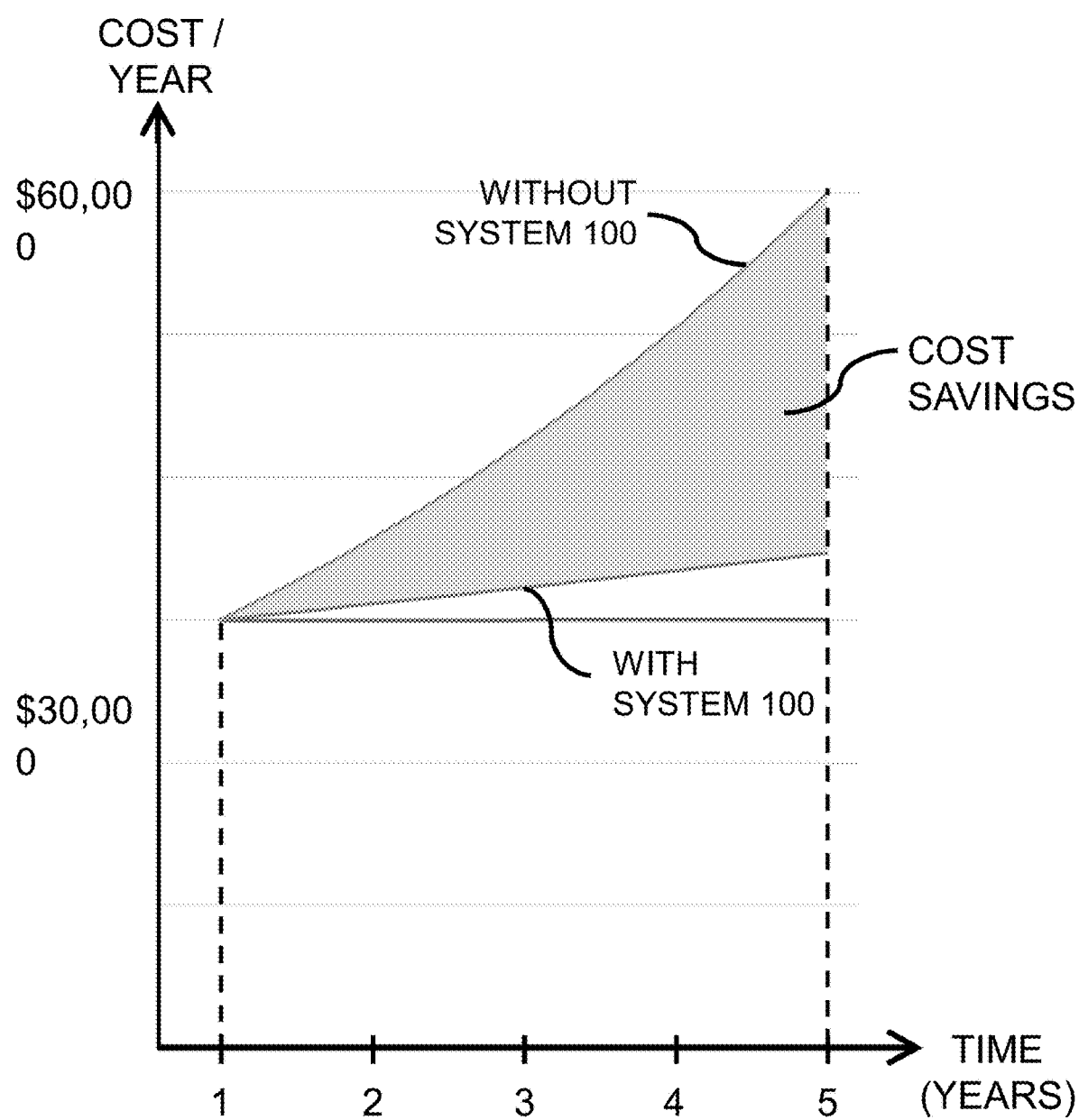
FIG. 11 is a diagram illustrating exemplary treatment cost savings produced by the system of the present disclosure.

Costs associated with treatment depend on the severity of the cognitive disease 223. As such, implementing the systems and methods of the present disclosure in connection with one or more of the medications and treatments described herein produces significant costs savings when compared to the costs of treatment without system 100. For example, FIG. 11 is a diagram illustrating the treatment cost savings produced by the system 100 of the present disclosure. As shown, such healthcare costs savings increase with patient age and cognitive disease severity once system 100 is added to standard of care (e.g., at year one (1) on the diagram shown in FIG. 11). Such costs savings are represented by the area between the two cost progression curves (e.g., with system 100 and without system 100). Costs can be for representative of cognitive medication administered with interaction with game cognitive training scenes 400, vs. cognitive medication alone. Additional savings stem from the fact that incidence of patients with Alzheimer's disease is growing. Further still, adding interaction with game scenes 400 of system 100 can lengthen the period of time over which cognitive medication 144 remains beneficial to the patient 17.

Figure 12:
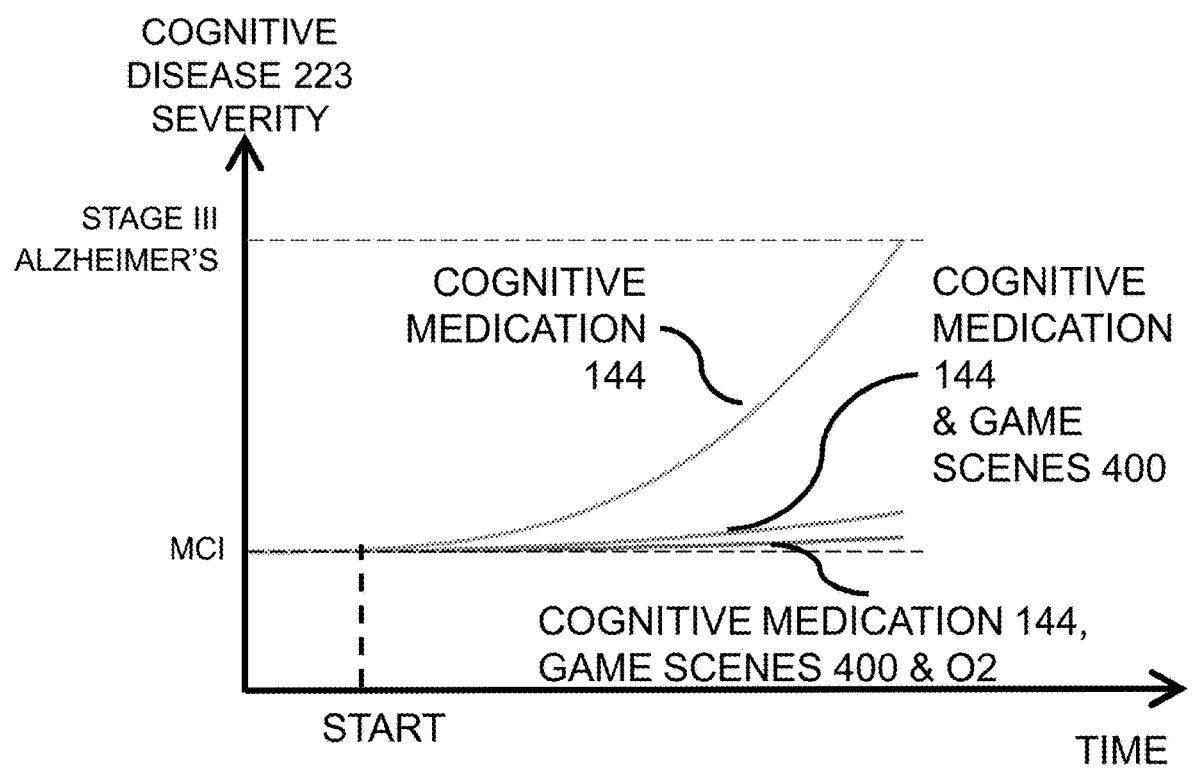
FIG. 12 is a diagram illustrating efficacy of the system of the present disclosure on the progression of Alzheimer's Disease.

FIG. 12 is a diagram illustrating the effect of the system 100 of the present disclosure on the progression of Alzheimer's disease from MCI to stage III (advanced stage). As shown, systems 100 utilizing cognitive medication 144 and therapeutic game scenes 400, with added oxygen to insure sufficient brain oxygenation 431 results in less severity of the cognitive disease 223 over time, as compared to systems 100 which utilize cognitive medication 144 and therapeutic game scenes 400, in the absence of sufficient brain oxygenation 431. In both cases, there is a substantially smaller increase in the severity of cognitive disease 223 over time, compared to the increase in the severity of cognitive disease 223 when only cognitive medication 144 is taken.

Figure 13:
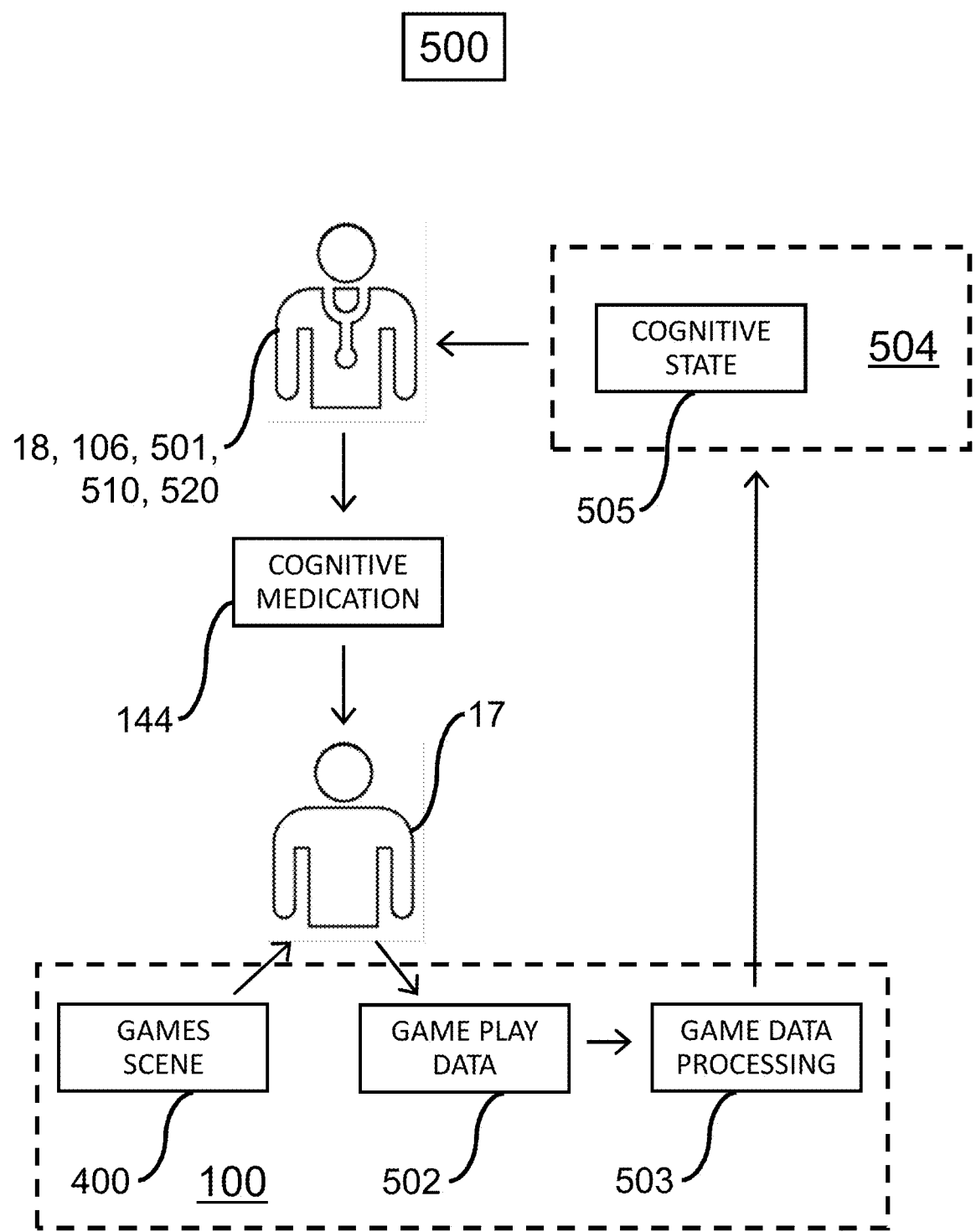
FIG. 13 is a diagram illustrating a method for treating a cognitive disease according to the present disclosure.

FIG. 13 is a diagram illustrating a method 500 for treating a cognitive disease, according to some aspects of the present disclosure. More specifically, FIG. 13 illustrates a method 500 for utilizing therapeutic game scenes 400 wherein a person 501 determines a dose of a cognitive medication 144 to be administered to the patient 17. The person 501 may be a person assisting in the care of the patient 17 such as a clinician 106 or caregiver 18, a researcher 510 studying cognitive medication 144, or other person 520 involved in determining the dosage of a cognitive medication 144 for the patient 17. The patient 17 receives a cognitive medication 144 as well as therapeutic game scenes 400 provided by the system 100. The system 100 obtains game play data 502 from the patient's 17 interaction with game scenes 400. The system 100 performs game data processing 503 and produces an output 504. The output 504 contains information on the patient's 17 cognitive state 505. The cognitive state 505 can include results of the system's 100 game data processing 503 including the patient's 17 cognitive aptitude, emotional disposition, impact of the cognitive medication 144 on the patient 17, adverse side effects of the cognitive medication 144 on the patient 17, and other data acquired by the system 100 during the patient's 17 interaction with the system 100 during gameplay. According to some aspects of the present disclosure, the output 504 can include data on the cognitive improvement 222 of the patient 17 utilizing the system 100.

The output 504 can be received by a person 501, 510, 520, 18. One or more of the persons 501 510, 520, 18 can utilizes the output 504 to modify the dosage of the cognitive medication 144. Utilization of the output 504 allows for titration of the cognitive medication 144, allowing for a reduction in dosages of the cognitive medication 144, a reduction in side effects of the cognitive medication 144, or an extension of the duration over which the cognitive medication 144 shows efficacy for the patient 17.

Figure 14:
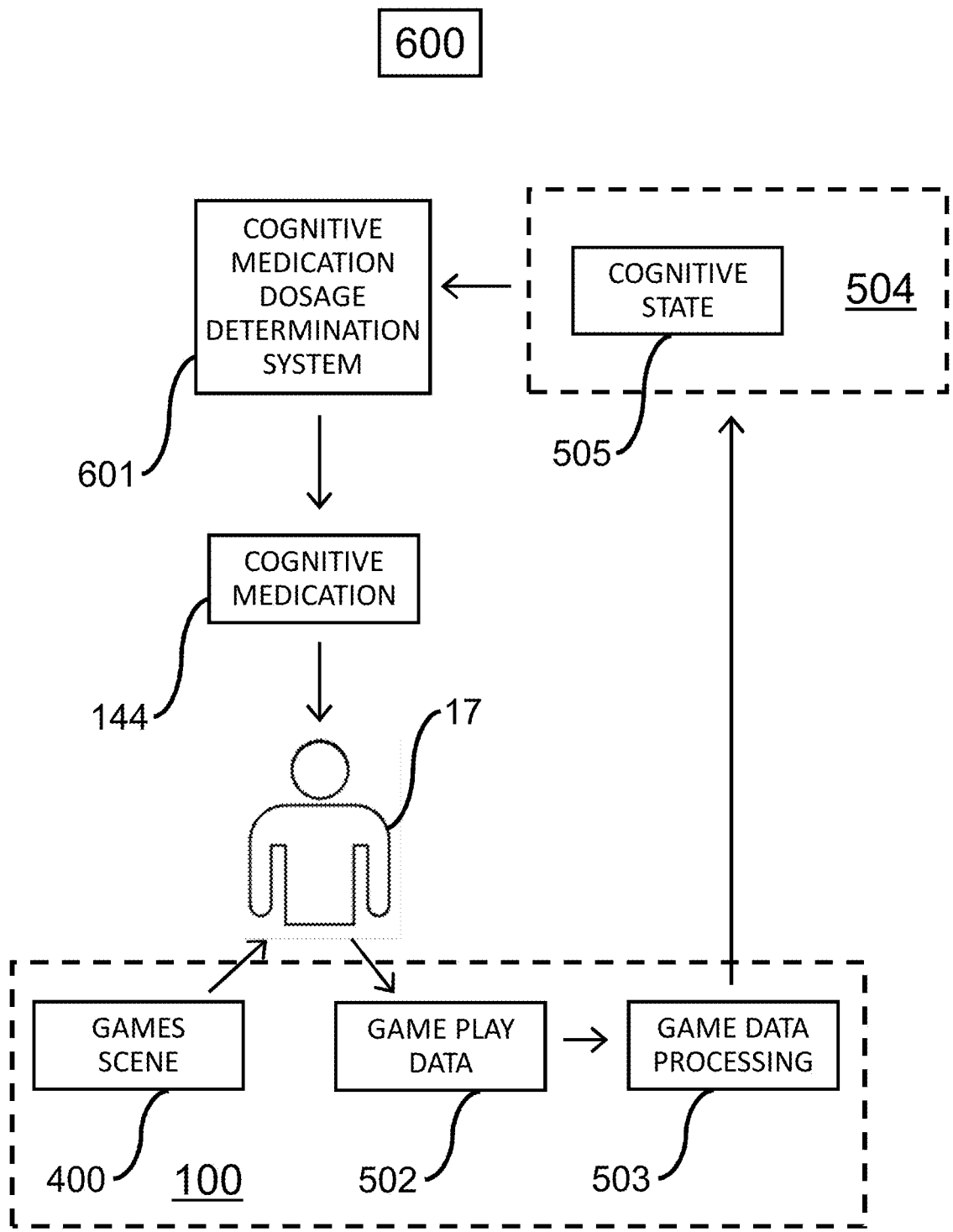
FIG. 14 is a diagram illustrating a method for treating a cognitive disease according to the present disclosure.

FIG. 14 is a diagram illustrating a method 600 for treating a cognitive disease, according to some aspects of the present disclosure. Method 600 is similar to method 500, discussed in connection with FIG. 13, except for the distinctions noted herein. More specifically, FIG. 14 depicts method 600, in which the person 501 of method 500 is replaced with a cognitive medication dosage determination system 601. Cognitive medication dosage determination system 601 can receive the output 504 to determine a dosage of the cognitive medication 144. The cognitive medication dosage determination system 601 can utilize machine learning, artificial intelligence software, or the like, together with patient information and output 504, in determining the correct dosage of the cognitive medication 144 for the patient 17. According to other aspects of the present disclosure, system 601 can automatically switch the type of cognitive medication 144 used to treat the patient 17.

Exemplary cognitive medications can include, but are not limited to, donepezil (marketed under the brand name Aricept®), which is approved to treat all stages of Alzheimer's disease, and galantamine (marketed under the brand name Razadyne®), which is approved for mild-to-moderate stages of Alzheimer's Disease. For example, with regard to donepezil, an initial dose of 5 mg per day is recommended, which is thereafter increased to a maintenance dose. For mild to moderate Alzheimer's disease, a maintenance dose of 10 mg per day of donepezil is recommended, while for cases of moderate to severe Alzheimer's disease, the maintenance dose is increased to 23 mg per day after the patient has been on a dose of 10 mg per day for at least three (3) months. With regard to galantamine, the recommended initial dose is 8 mg per day, which is increased to a maintenance dose that is between 16 and 24 mg orally once a day based on clinical benefit and tolerability. However, when combined with the cognitive training systems and methods described herein, the dosages of these cognitive medications can be reduced. For example, a patient prescribed 23 mg per day of donepezil can have their dosage reduced to 10 mg per day when administered in connection with the cognitive training systems of the present disclosure. Similarly, a patient prescribed 24 mg a day of galantamine (e.g., or another dosage on the upper end of the recommended range) can have their dosage reduced to 16 mg per day (e.g., or another dosage on the lower end of the recommended range) when administered in connection with the cognitive training systems of the present disclosure. Further still, the systems and methods described herein (e.g., in connection with FIGS. 13 and 14) can recommend that a patient switch from donepezil to galantamine, or vice versa, if the system determines that the other cognitive medication is more beneficial (e.g., increased efficacy, lower side effects, etc.) for the patient.

Having thus described the systems and methods in detail, it is to be understood that the foregoing description is not intended to limit the spirit or scope thereof. It will be understood that the embodiments of the present disclosure described herein are merely exemplary and that a person skilled in the art may make any variations and modification without departing from the spirit and scope of the disclosure. All such variations and modifications, including those discussed above, are intended to be included within the scope of the disclosure.

What is claimed is:

1. A method for providing cognitive therapy to a patient, comprising the steps of:
    providing a head mounted device wearable by a patient, a testing display configured to present one or more cognitive training scenes to the patient, one or more controllers enabling the patient to interact with the one or more cognitive training scenes, a cognitive engagement detection device configured to detect cognitive engagement of the patient, and one or more processors in communication with the head mounted device, the testing display, the one or more controllers, and the cognitive engagement detection device, the cognitive engagement detection device comprising one or more sensors;
    providing, by the one or more processors, a cognitive medication dosage for a patient on a patient information display device;
    generating, by the one or more processors, one or more cognitive training scenes and displaying the one or more cognitive training scenes on the testing display;
    receiving data indicative of the cognitive state of the patient from a memory of the cognitive engagement detection device based on input provided by at least one of the one or more sensors, the data indicative of the cognitive state comprising data indicative of cognitive engagement and data indicative of cognitive fatigue, the cognitive engagement being a mental effort of the patient learning to interact with the one or more cognitive training scenes and success in performing gaming tasks related to the one or more cognitive training scenes, the cognitive fatigue being an impaired sensory and attention-related mental processing of the patient;
    receiving information from the one or more controllers;
    determining the cognitive engagement and cognitive fatigue of the patient based at least in part on the data received from the cognitive engagement detection device;
    determining performance of the patient interacting with the one or more cognitive training scenes based on the information received from the one or more controllers;
    determining, via the one or more processors, a modification of the cognitive medication dosage or cognitive medication type based on the cognitive engagement, cognitive fatigue, a type of the patient, and the performance of the patient; and
    displaying the modification of the cognitive medication dosage or cognitive medication type on the patient information display device.

2. The method of claim 1, wherein the cognitive state of the patient includes one or more of cognitive improvement of the patient, cognitive aptitude of the patient, emotional disposition of the patient, efficacy of the cognitive medication on the patient, and adverse side effects of the cognitive medication on the patient.

3. The method of claim 1, comprising the step of receiving data indicative of the cognitive state of the patient at a medication dosage determination system.

4. The method of claim 3, wherein the step of modifying the cognitive medication dosage is performed by the medication dosage determination system.

5. The method of claim 4, wherein the medication dosage determination system processes data indicative of the cognitive state of the patient using one or more of machine learning or artificial intelligence algorithms executed by the one or more processors.

6. The method of claim 5, wherein modifying the cognitive medication dosage or cognitive medication type is based on the cognitive engagement, cognitive fatigue, the type of the patient, the performance of the patient, and patient information.

7. The method of claim 6, wherein the step of modifying the cognitive medication dosage, includes identifying a second cognitive medication and dosage.

8. The method of claim 7, comprising providing the second cognitive medication and dosage to the patient.

9. The method of claim 1, wherein the one or more sensors comprise at least one of: a skin temperature sensor, a head orientation sensor, and/or a blink detection sensor.

10. The method of claim 1, further comprising a computational cognitive medication dosage determination system.

11. The method of claim 10, further comprising: utilizing one or more of machine learning, artificial intelligence means, patient information, and/or patient cognitive improvement data for at least one of: determining a correct dosage recommendation of the cognitive medication, and/or modifying the type or dosage of the cognitive medication recommendation for the patient.

* * * * *